US 11,013,520 B2

(12) United States Patent
Gareiss et al.

(10) Patent No.: US 11,013,520 B2
(45) Date of Patent: May 25, 2021

(54) REAMER SHAFT EXTENSION ASSEMBLY

(71) Applicant: Avalign Technologies, Inc., Bannockburn, IL (US)

(72) Inventors: Warren Scott Gareiss, Warsaw, IN (US); Ryan Michael Ratkowski, Churubusco, IN (US)

(73) Assignee: Avalign Technologies, Inc., Bannockburn, IL (US)

( * ) Notice: Subject to any disclaimer, the term of this patent is extended or adjusted under 35 U.S.C. 154(b) by 286 days.

(21) Appl. No.: 16/160,400

(22) Filed: Oct. 15, 2018

(65) Prior Publication Data
US 2020/0113585 A1 Apr. 16, 2020

(51) Int. Cl.
*A61B 17/16* (2006.01)
*A61B 50/33* (2016.01)
*A61B 17/00* (2006.01)

(52) U.S. Cl.
CPC .......... *A61B 17/1659* (2013.01); *A61B 50/33* (2016.02); *A61B 2017/00477* (2013.01); *A61B 2017/00526* (2013.01)

(58) Field of Classification Search
CPC . A61B 17/1617; A61B 17/1675; A61B 17/16; A61B 17/1631; A61B 17/1637; A61B 17/1659; A61B 17/1697; B27G 15/00
USPC ............... 606/79–85; 408/199–200
See application file for complete search history.

(56) References Cited

U.S. PATENT DOCUMENTS

| 4,706,659 | A | * | 11/1987 | Matthews | ............... | B23B 31/08 |
| | | | | | | 606/80 |
| 5,203,595 | A | * | 4/1993 | Borzone | ............ | A61B 17/1631 |
| | | | | | | 285/325 |
| 6,447,518 | B1 | * | 9/2002 | Krause | ................. | A61B 17/164 |
| | | | | | | 606/80 |
| 6,468,279 | B1 | * | 10/2002 | Reo | ......................... | A61B 17/16 |
| | | | | | | 600/567 |
| 2010/0151161 | A1 | * | 6/2010 | Da Rolo | ............ | A61B 17/1631 |
| | | | | | | 606/80 |
| 2012/0065638 | A1 | * | 3/2012 | Moore | ............... | A61B 17/7225 |
| | | | | | | 606/62 |
| 2013/0090690 | A1 | * | 4/2013 | Walsh | ................ | A61B 17/7023 |
| | | | | | | 606/257 |

(Continued)

OTHER PUBLICATIONS

Zimmer, Inc. Orthopaedic Reusable Devices. Dec. 31, 2015. [retrieved on Nov. 19, 2019]. Retrieved from internet: URL:https://www.zimmerblomet.com/content/dam/zimmer-biomet/medical-professionas/support/reusable-device-reprocessing-Instructions/orthopaedlc-reusable-devIces,pdf [entire document].

(Continued)

*Primary Examiner* — Jessica Weiss
(74) *Attorney, Agent, or Firm* — BakerHostetler

(57) ABSTRACT

A reamer shaft extension includes a shaft positioned between a first end having a first coupling and a second end having a second coupling. The first coupling of each reamer shaft extension is selectively couplable with the second coupling of another reamer shaft extension such that a select amount of reamer shaft extensions are assembled together to form a reamer shaft extension assembly for use in a reaming procedure. Each reamer shaft extension further has a sufficiently short enough length such that each reamer shaft extension is insertable within a sterilization tray for use in a sterilization procedure.

19 Claims, 8 Drawing Sheets

(56) References Cited

U.S. PATENT DOCUMENTS

| | | | | |
|---|---|---|---|---|
| 2013/0150860 A1* | 6/2013 | Sidebotham | ....... | A61B 17/1666 606/81 |
| 2015/0073417 A1* | 3/2015 | Norton | ............... | A61B 17/1617 606/80 |
| 2016/0345986 A1* | 12/2016 | Slobitker | ........... | A61B 17/1642 606/80 |
| 2019/0069908 A1* | 3/2019 | Zilberman | ......... | A61B 17/1631 428/34.1 |

OTHER PUBLICATIONS

International Search Report and Written Opinion issued in PCT/US2019/056025, dated Dec. 18, 2019.

* cited by examiner

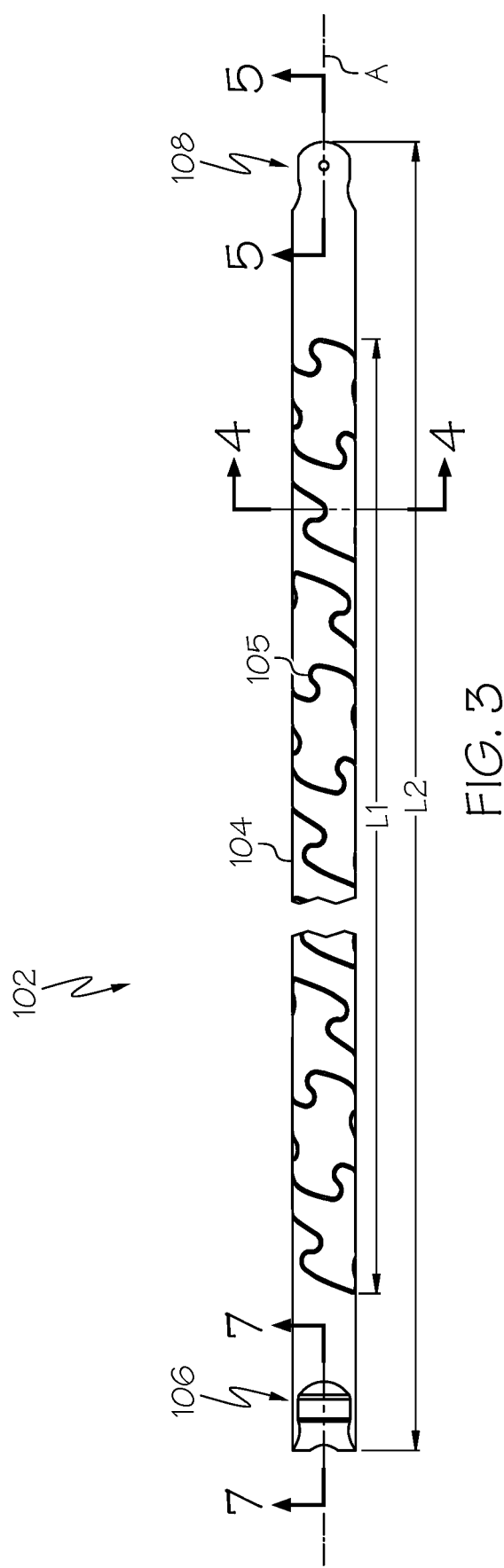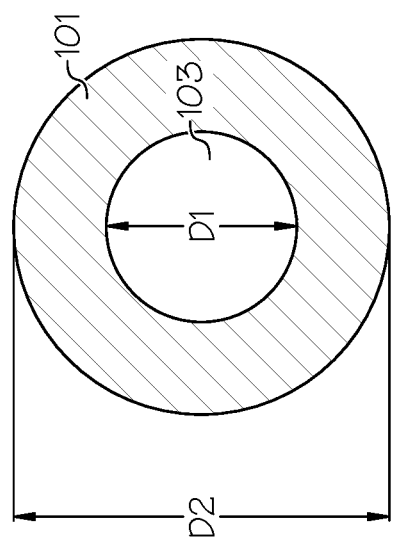
FIG. 3
FIG. 4

REAMER SHAFT EXTENSION ASSEMBLY

BACKGROUND

In some instances, an anatomic region of the human anatomy may need to be repaired and/or replaced due to injury, stress, degenerative health issues, or various other problems. To perform such a repair and/or replacement on the affected anatomical region, it may be necessary to cut or remove portions of bone and associated tissue matter with a reaming device, or reamer, as shown in FIG. 1. A reamer (50) typically includes a continuous reamer shaft (52) with a reamer tip (54) at the end of the reamer shaft (52) used to cut or bore into the inner canal of a long bone (2) (e.g., femur, tibia, etc.) to clean and create space for an implant to be received and/or to help mend a fractured bone. Before the reaming process, a wire (40) is typically inserted into the space to serve as a guide for receiving the reamer shaft (52).

A reamer shaft generally requires frequent sterilization. During the sterilization process, a sterilization tray may be used to hold the medical equipment being sterilized. Typical dimensions of a sterilization tray are about ten by twenty-one inches in length/width with a depth of about three inches. Because the reamer shaft is of a sufficient length to bore through a long bone, the reamer shaft may be too long to fit into a standard sterilization tray. For instance, FIG. 1 shows that the reamer shaft (52) is longer than the sterilization tray (10). This may add complexity and/or costs during the sterilization of a reamer shaft. Accordingly, it may be desirable to provide an extendable reamer shaft that may fit into a standard sterilization tray while having a sufficient length to drill through a long bone.

While a variety of reamer shafts have been made and used, it is believed that no one prior to the inventors has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 3 depicts a side elevational view of a reamer shaft extension of the reamer shaft extension assembly of FIG. 2.

FIG. 4 depicts a cross-sectional view of a shaft of the reamer shaft extension of FIG. 3 taken along line 4-4 of FIG. 3.

Figure 1:
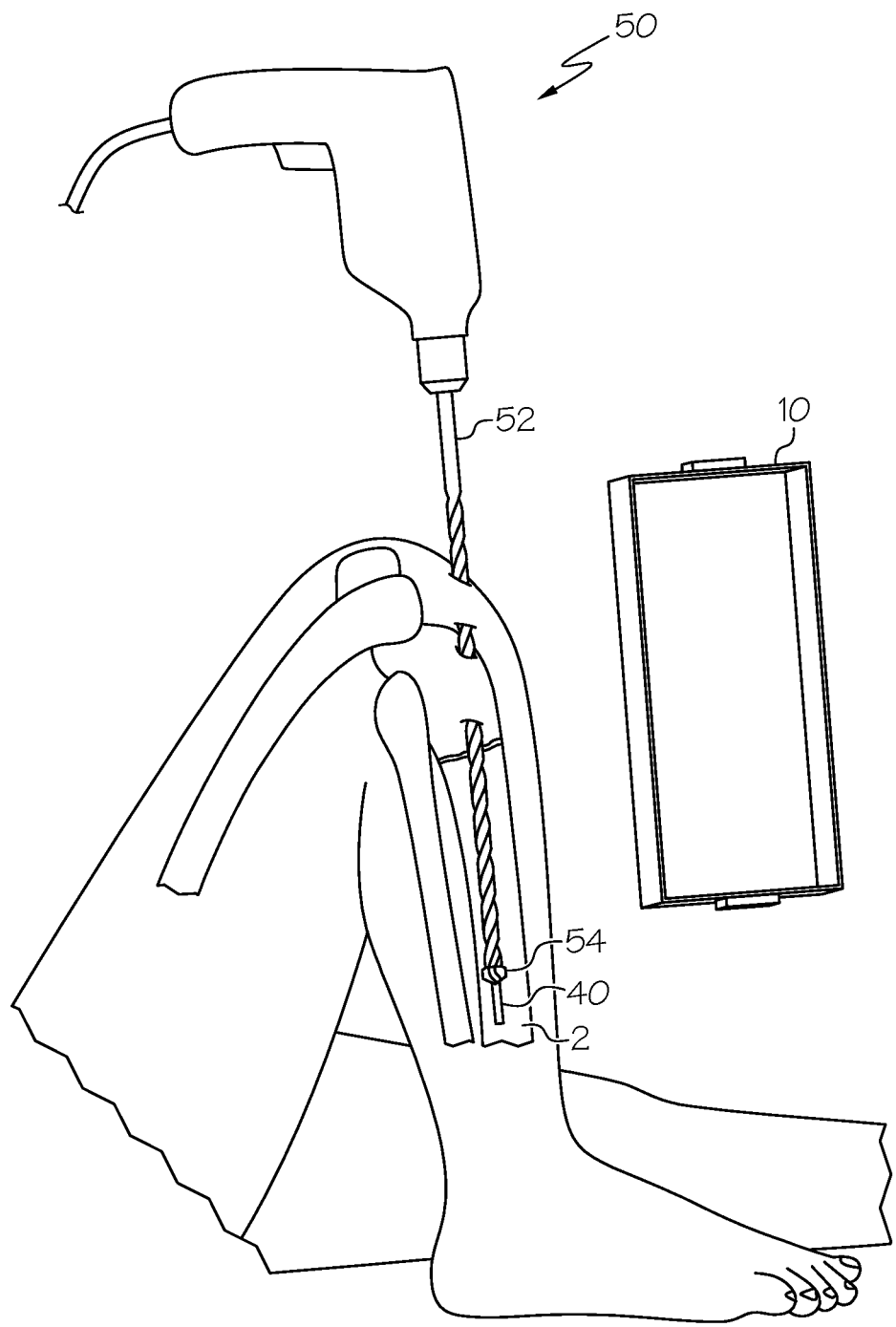
FIG. 1 depicts a perspective view of a prior art reamer being used during a surgical procedure alongside a standard sterilization tray.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

In some instances, it may be desirable to provide a reamer shaft extension assembly having more than one reamer shaft extension. Accordingly, the reamer shaft extensions may be coupled together to form a reamer shaft extension assembly having a sufficient length capable of drilling through a long bone in an anatomic region of the human anatomy. The length of the reamer shaft extension assembly may thereby be selectively adjustable based on the number of reamer shaft extensions used. The reamer shaft extension assembly may then be disassembled such that each reamer shaft extension may fit within a standard sterilization tray to more easily and efficiently sterilize each reamer shaft extension. Such a reamer shaft extension assembly is discussed in more detail below.

I. Reamer Shaft Extension Assembly

Figure 2:
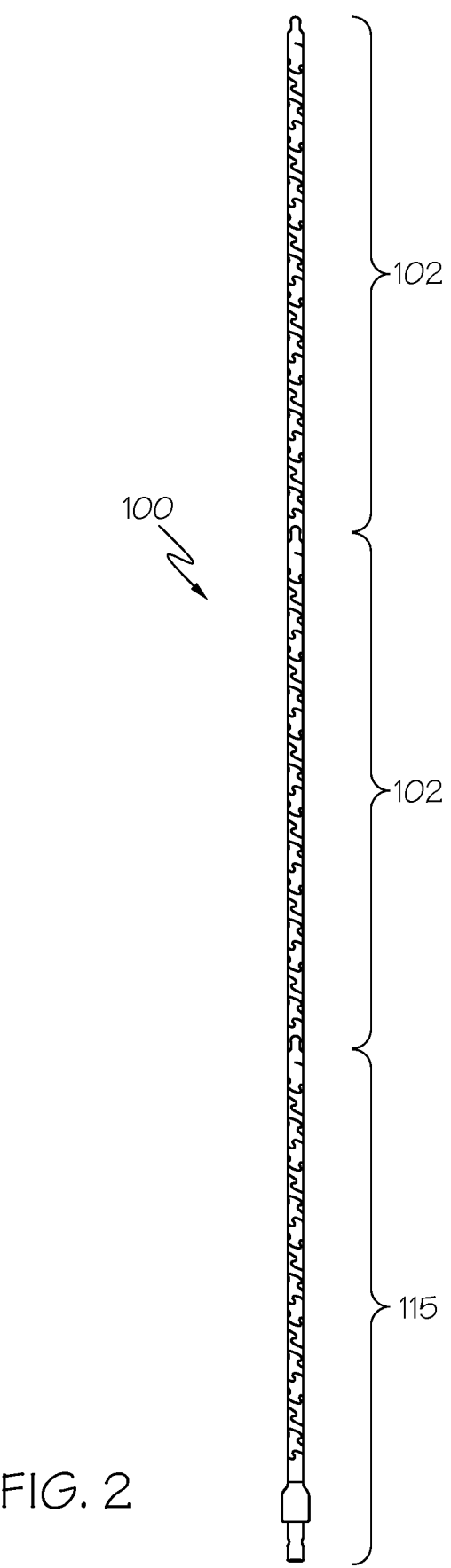
FIG. 2 depicts a side elevational view of an embodiment of a reamer shaft extension assembly.

Referring to FIG. 2, a reamer shaft extension assembly (100) is shown having more than one reamer shaft extension (102) coupled together and attached to a reamer shaft base (115). Reamer shaft base (115) includes a shank disposed at one end for coupling with a drill and a reamer tip (54) disposed at a second end. While the illustrated embodiment shows two reamer shaft extensions (102) coupled together with a reamer shaft base (115), any other suitable number of reamer shaft extensions (102) may be assembled. For instance, the length of the reamer shaft extension assembly (100) may vary depending on the selected number of reamer shaft extensions (102) used. The reamer shaft extension assembly (100) may also be selectively adjustable by adding and/or removing a desired number of reamer shaft extensions (102) from the reamer shaft extension assembly (100). Still other suitable configurations for the reamer shaft extension assembly (100) will be apparent to one with ordinary skill in the art in view of the teachings herein.

A reamer shaft extension (102) of the reamer shaft extension assembly (100) is shown in more detail in FIGS. 3-4. Each reamer shaft extension (102), as well as reamer shaft base (115) comprises a shaft (104) positioned between a first end (108) and a second end (106). The shaft (104) comprises a side wall (101) that defines an opening (103) extending along a longitudinal axis (A) of the shaft (104), whereby when reamer shaft extensions (102) and/or reamer shaft base (115) are connected, each opening (103) in the assembly is generally coaxial with one another in an unflexed state.

The opening (103) allows the reamer shaft extension assembly (100) to be positioned over a guidewire during a surgical procedure. The side wall (101) of the shaft (104) has a substantially constant diameter. For instance, the shaft (104) may have an inner diameter ($D_1$) of between about 0.0094 inches and about 0.129 inches and an outer diameter ($D_2$) of between about 0.228 inches and about 0.3 inches, though other suitable dimensions may be used. The length ($L_1$) of the shaft (104) may be between about 8.48 and about 8.52 inches and the length ($L_2$) of the reamer shaft extension (102) may be less than about 23 inches, such as between about 9.84 and about 9.86 inches, though other suitable dimensions may be used. Alternatively, the length (L1) of the shaft (104) may have a length of between 75% and 90% of the length (L2). Accordingly, each reamer shaft extension (102) has a length that is less than a standard sterilization tray (10). In the illustrated embodiment, the shaft (104) comprises a pattern of cutouts (105) such that the shaft (104) is flexible about these cutouts (105). It should be noted that these cutouts (105) are merely optional. In some other versions, the shaft (104) may comprise a flexible material without the cutouts (105), or the shaft (104) may be rigid. Still other suitable configurations for the shaft (104) will be apparent to one with ordinary skill in the art in view of the teachings herein.

Figure 5:
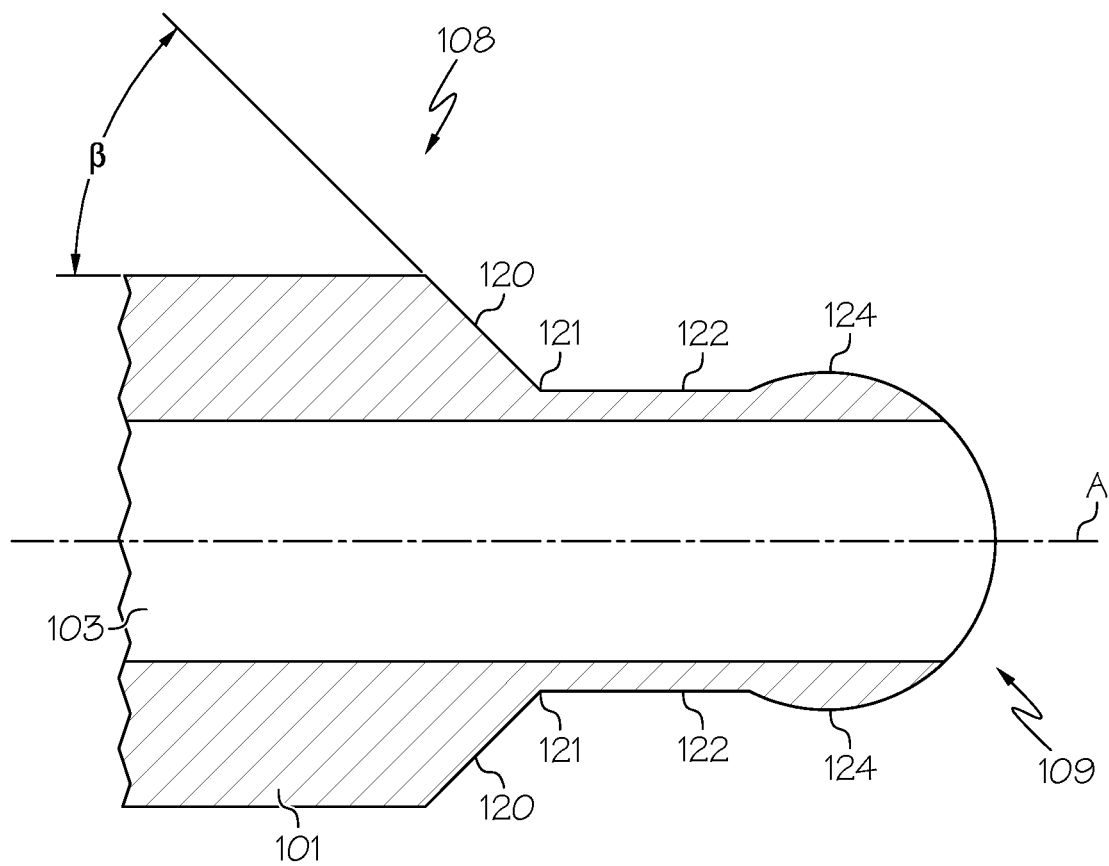
FIG. 5 depicts a cross-sectional view of a first end of the reamer shaft extension of FIG. 3 taken along line 5-5 of FIG. 3.
Figure 6:
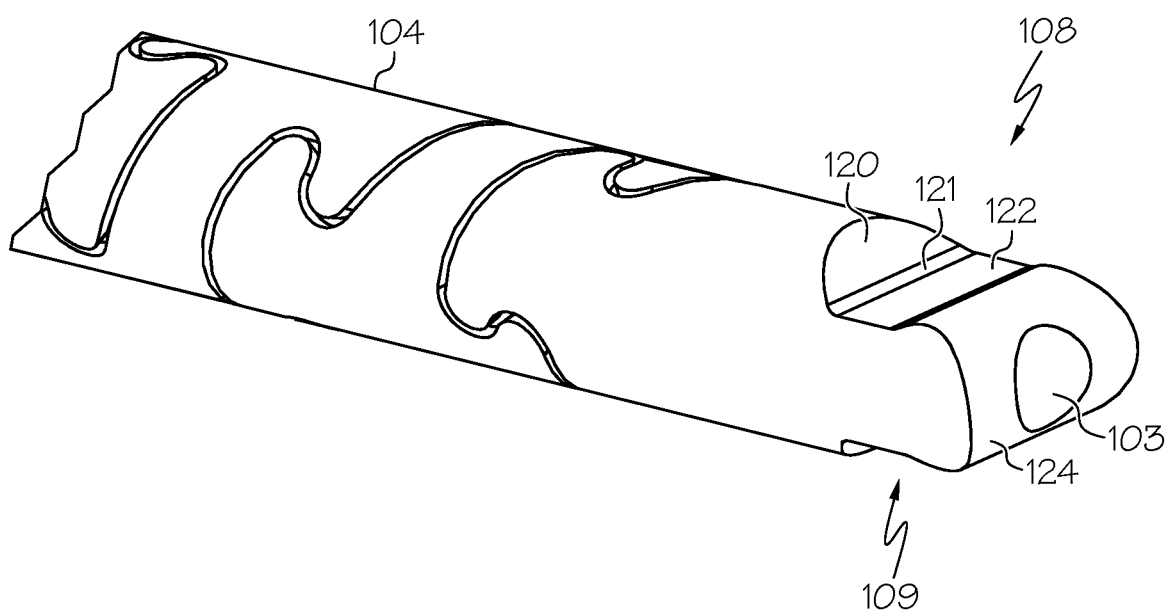
FIG. 6 depicts a perspective view of the first end of the reamer shaft extension of FIG. 3.

As shown in FIG. 2, each first end (108) of the reamer shaft extension (102) or reamer shaft base (115) is couplable with each second end (106) of the reamer shaft extension (102). The first end (108) of the reamer shaft extension (102) comprises a male dovetail (109) as shown in FIGS. 5-6. The male dovetail (109) comprises a tapered wall (120) extending downwardly and outwardly from a top portion and bottom portion of the side wall (101) of the shaft (104). For instance, each tapered wall (120) may extend at an angle (β) relative to the side wall (101). The angle (β) may be about 42.5°, though other suitable dimensions may be used. In the illustrated embodiment, a flange (122) then extends outwardly from the tapered walls (120) such that the flange (122) is substantially parallel with the longitudinal axis (A) of the reamer shaft extension (102). The flange (122) may have a thickness of between about 0.154 inches and about 0.158 inches, though other suitable dimensions may be used. A corner (121) is thereby formed between the flange (122) and each tapered wall (120). Each corner (121) may have a radius of about 0.03 inches, but other suitable dimensions may be used. A rounded end (124) then extends outwardly from the flange (122) such that the rounded end (124) has a greater thickness than the flange (122). The rounded end (124) may have a radius of between about 0.178 inches and about 0.182 inches, though other suitable dimensions may be used. The male dovetail (109) may thereby have a length of between about 0.228 inches and about 0.23 inches, but other suitable dimensions may be used.

Figure 7:
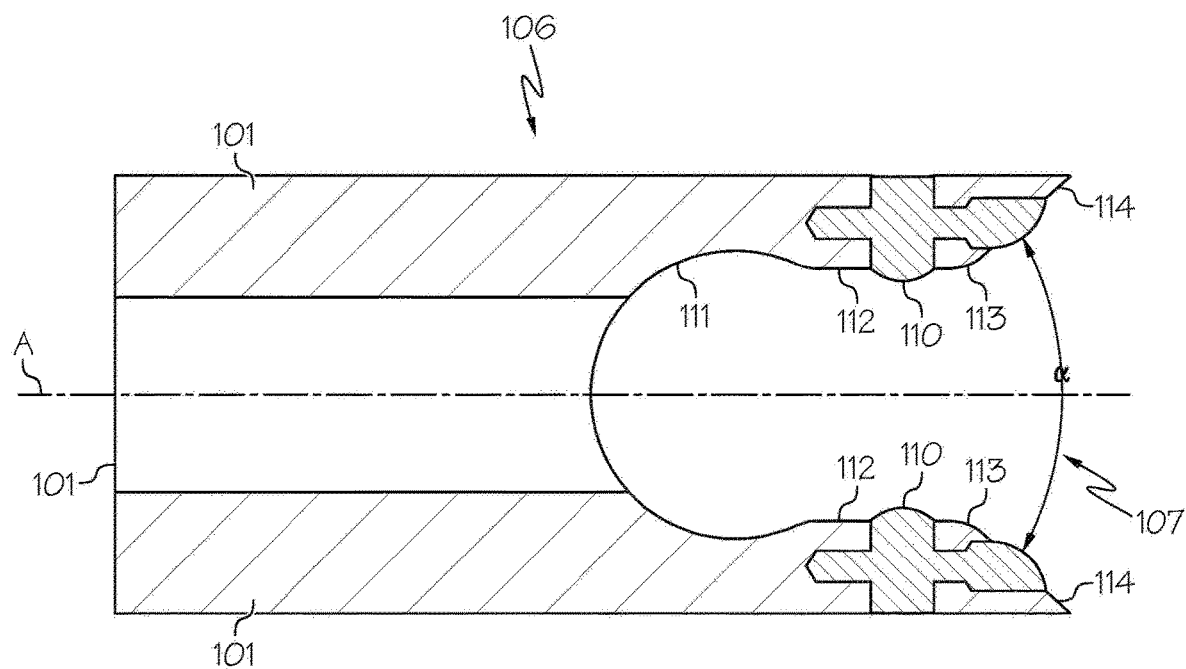
FIG. 7 depicts a cross-sectional view of a second end of the reamer shaft extension of FIG. 3 taken along line 7-7 of FIG. 3.
Figure 8:
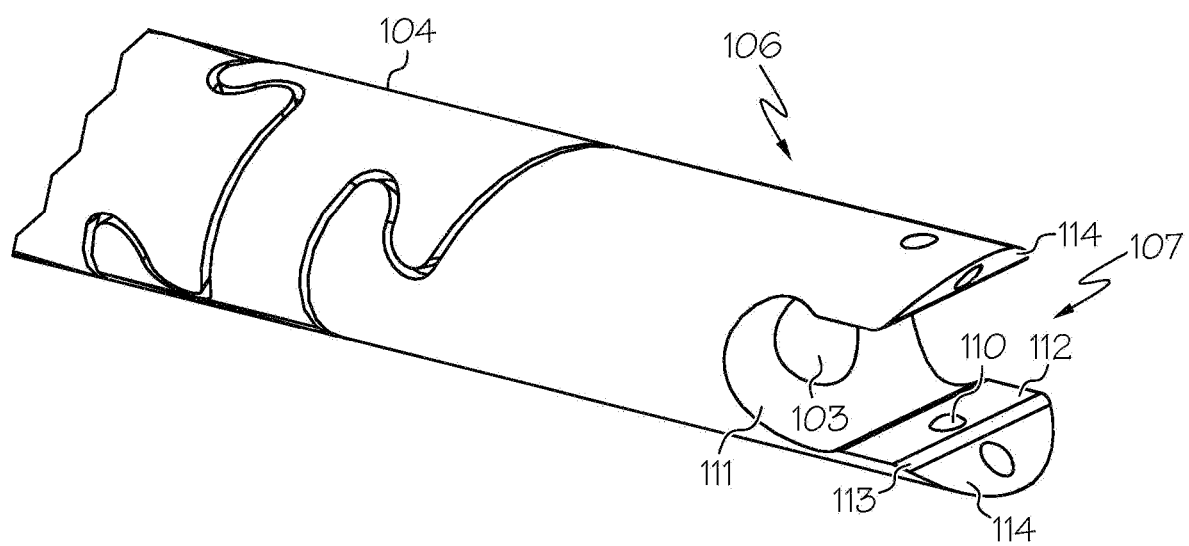
FIG. 8 depicts a perspective view of the second end of the reamer shaft extension of FIG. 3.

The second end (106) of the reamer shaft extension (102) comprises a female dovetail (107), shown in FIGS. 7-8, that is couplable with the male dovetail (109) described above. The female dovetail (107) comprises a tapered wall (114) extending inwardly and downwardly from a top portion and bottom portion of the side wall (101) of the reamer shaft extension (102). The tapered walls (114) extend at an angle that corresponds with the tapered walls (120) of the male dovetail (109). In the illustrated embodiment, an about 85° angle is formed between the tapered walls (114), but other suitable dimensions may be used. A channel (112) then extends inwardly from the tapered walls (114) such that the channel (112) is substantially parallel with the longitudinal axis (A) of the reamer shaft extension (102). The channel (112) thereby corresponds with the flange (122) of the male dovetail (109). The channel (112) may define a gap that is about 0.162 inches thick, but other suitable dimensions may be used. A corner (113) formed between the channel (112) and each tapered wall (114) may be rounded with a radius of about 0.03 inches, but other suitable dimensions may be used. In the illustrated embodiment, each surface of the channel (112) includes a retention insert (110) projecting into the channel (112). Each retention insert (110) may be formed from a thermoplastic material, or other suitable material, that slightly compresses when the male dovetail (109) is received within the female dovetail (107) such that the retention insert (110) is configured to hold the position of the male dovetail (109) relative to the female dovetail (107). A rounded recess (111) then extends inwardly from the channel (112) that corresponds with the rounded end (124) of the male dovetail (109). In the illustrated embodiment, the rounded recess (111) has a radius of about 0.185 inches, but other suitable dimensions may be used.

Accordingly, the male dovetail (109) of the first end (108) can be inserted into the female dovetail (107) of the second end (106) to couple the first end (108) of one reamer shaft extension (102) with the second end (106) of another reamer shaft extension (102). This extension may then be coupled with reamer shaft base (115) for insertion into a drill, such as drill (50) of FIG. 1. For instance, the rounded end (124) of the male dovetail (109) can be inserted through the channel (112) and into the rounded recess (111) of the female dovetail (107). As the rounded end (124) is inserted within the female dovetail (107), the tapered walls (114) of the female dovetail (107) are configured to guide the rounded end (124) into the channel (112). Because the channel (112) of the illustrated embodiment has a smaller diameter than the thickness of the rounded end (124), the channel (112) may slightly flex outward while the rounded end (124) is translated through the channel (112). The rounded end (124) may thereby be positioned within the rounded recess (111) of the female dovetail (107) to align the channel (112) with the flange (122) and the tapered walls (114) of the female dovetail (107) with the tapered walls (120) of the male dovetail (109). The channel and/or the retention inserts (110) may be friction fit with the flange (122) to maintain the position of the male dovetail (109) within the female dovetail (107). Still other suitable configurations for coupling the reamer shaft extensions (102) will be apparent to one with ordinary skill in the art in view of the teachings herein.

II. Method of Using a Reamer Shaft Extension Assembly

The reamer shaft extension assembly (100) may be prepared for use in a medical procedure, such as reaming procedure, by assembling two or more reamer shaft extensions (102) together and coupling this extension with a reamer shaft base (115), as shown in FIG. 2, and connecting reamer tip (54) (FIG. 1) onto the distal end. Accordingly, the male dovetail (109) of a first end (108) of one reamer shaft extension (102) (or reamer shaft base (115) may be inserted into the female dovetail (107) of a second end (106) of another reamer shaft extension (102) as described above. While the illustrated embodiment shows two reamer shaft extensions (102) assembled with a reamer shaft base (115), any suitable number of reamer shaft extensions (102) may be used to provide the desired length for the reamer shaft extension assembly (100). Accordingly, the reamer shaft extensions (102) and reamer shaft base (115) may be coupled together to form a reamer shaft extension assembly (100) having a sufficient length to be capable of drilling through a long bone of an anatomic region of the human anatomy. The length of the reamer shaft extension assembly (100) may also be selectively adjustable at a medical facility based on the number of reamer shaft extensions selected.

As shown in FIG. 2, once the desired number of reamer shaft extensions (102) are coupled together with reamer shaft base (115) to form the reamer shaft extension assembly (100), the shaft (104) of each reamer shaft extension (102) is aligned such that the reamer shaft extension assembly (100) has a substantially constant diameter along the length of the reamer shaft extension assembly (100). Accordingly, the connection point between each of the first and second ends (106, 108) provide a substantially constant diameter such that each connection point does not add a larger diameter feature that may create a higher pressure below the connection point. The connection point between each of the first and second ends (106, 108) is further configured to maintain the position of one reamer shaft extension (102) relative to another reamer shaft extension (102), and in particular when torque is applied to the reamer shaft extension assembly (100) during operation of the reamer shaft extension assembly (100).

Figure 9:
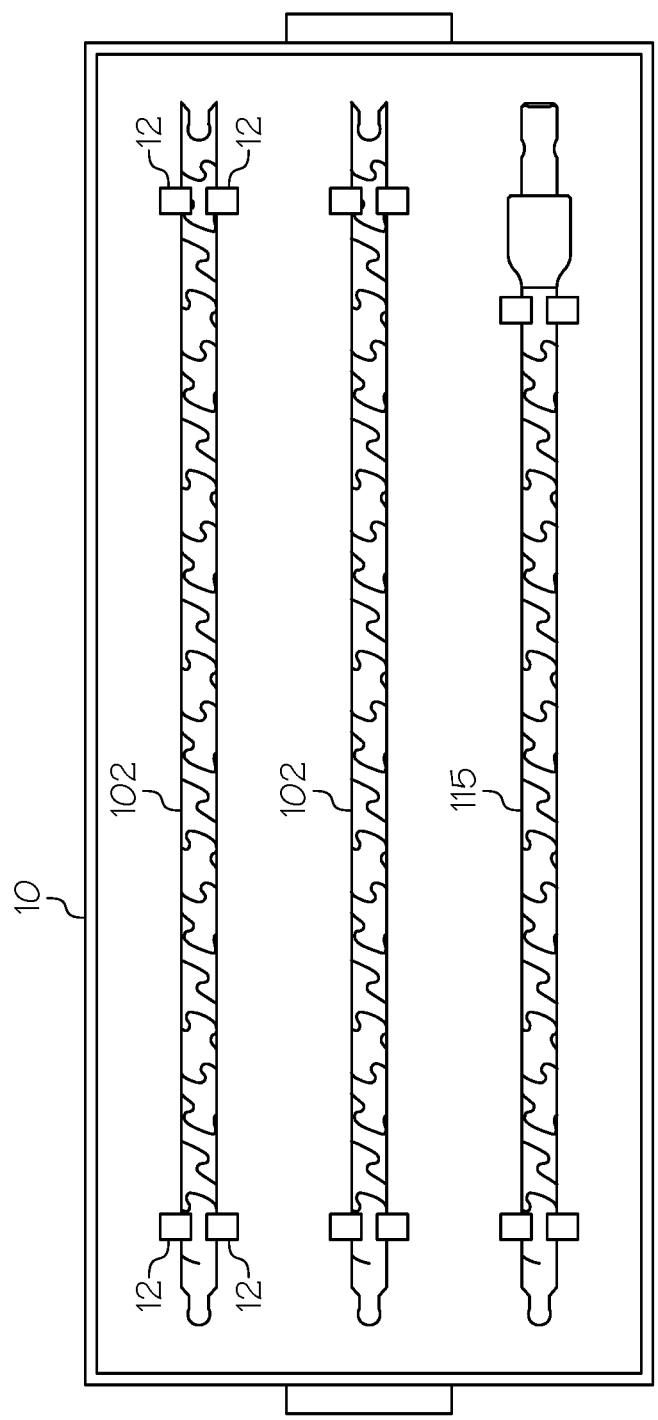
FIG. 9 depicts a top plan view of the reamer shaft extension assembly of FIG. 2 disassembled and positioned in a sterilization tray.

For a medical procedure, a reamer tip, such as reamer tip (54) shown in FIG. 1, may be coupled with one end of the reamer shaft extension assembly (100). The reamer shaft extension assembly (100) may then be guided over a wire (40) and inserted within a bone (2) to perform reaming of the bone (2) as shown in FIG. 1. After the medical procedure, the reamer shaft extension assembly (100) may be disassembled and placed in a sterilization tray (10) for sterilizing, as shown in FIG. 9. For instance, each reamer shaft extension (102) may be pulled apart from the other reamer shaft extensions (102) and/or reamer shaft base (115) to remove the male dovetail (109) from the female dovetail (107) at the first and second ends (106, 108). Each reamer shaft extension (102) may then be placed in a standard sterilization tray (10). Accordingly, the length of each reamer shaft extension (102) is less than about 23 inches such that each reamer shaft extension (102) is configured to be shorter than the length of a standard sterilization tray (10). One or more reamer shaft extensions (102) and/or reamer shaft bases (115) may be placed in a single sterilization tray (10). In some versions, the sterilization tray (10) may comprise a pair of arms (12) configured to hold a portion of each reamer shaft extension (102) or reamer shaft base (115). Accordingly, the arms (12) may maintain the position of the reamer shaft extension (102) or reamer shaft base (115) in the sterilization tray (10) during sterilization. The reamer shaft extension assembly (100) can thereby be disassembled to provide a more efficient sterilization process. Still other suitable configurations for sterilizing the reamer shaft extension assembly (100) and/or reamer shaft base (115) will be apparent to one with ordinary skill in the art in view of the teachings herein.

The reamer shaft extension assembly may include any one or more of a reamer shaft base, a reamer shaft extension, and/or a reamer tip. For example, in some versions, reamer shaft extension assembly includes a reamer shaft base, a reamer tip, and one or more reamer shaft extensions. In other versions, reamer shaft extension assembly includes one or more reamer shaft extensions. In yet other versions, reamer shaft extension assembly includes a reamer shaft base along with any number of reamer shaft extensions.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A reamer shaft extension assembly comprising at least two reamer shaft extensions, wherein each reamer shaft extension comprises a first coupling at a first end and a second coupling at a second end, wherein the first coupling of one of the reamer shaft extensions is selectively couplable with the second coupling of the other reamer shaft extension such that the reamer shaft extension assembly has a substantially constant outer diameter along the length of the reamer shaft extension assembly.

EXAMPLE 2

The reamer shaft extension assembly of example 1, wherein the first coupling comprises a male dovetail, wherein the second coupling comprises a female dovetail corresponding to the male dovetail such that the male dovetail is insertable within the female dovetail.

EXAMPLE 3

The reamer shaft extension assembly of example 2, wherein the male dovetail comprises a flange and a rounded end extending from the flange, wherein the female dovetail comprises a channel and a rounded recess extending from the channel, wherein the flange is configured to be aligned within the channel and wherein the rounded end is configured to be aligned within the rounded recess.

EXAMPLE 4

The reamer shaft extension assembly of example 3, wherein the channel comprises at least one reaming head extending into the channel, wherein the at least one reaming head is configured to compress against the flange to hold the flange within the channel.

EXAMPLE 5

The reamer shaft extension assembly of any of the examples 2 through 4, wherein the male dovetail comprises a first pair of tapered walls and the female dovetail comprises a second pair of tapered walls corresponding to the first pair of tapered walls.

EXAMPLE 6

The reamer shaft extension assembly of any of the preceding examples, wherein the reamer shaft extension assembly comprises an opening extending through a longitudinal axis of the reamer shaft extension assembly.

EXAMPLE 7

The reamer shaft extension assembly of any of the preceding examples, wherein each reamer shaft extension comprises a length of less than about 23 inches.

EXAMPLE 8

The reamer shaft extension assembly of any of the preceding examples, wherein each reamer shaft extension is positionable in a sterilization tray for a sterilization process.

EXAMPLE 9

The reamer shaft extension assembly of any of the preceding examples, wherein a shaft positioned between the first end and the second end of each reamer shaft extension is flexible.

EXAMPLE 10

A reamer shaft extension assembly comprising: (a) a reamer shaft extension extending from a first end to a second end and having a length of less than 23 inches, the reamer shaft extension defining a first opening therethrough and comprising: (i) a male dovetail disposed at the first end of the reamer shaft extension, and (ii) a female dovetail disposed at the second end of the reamer shaft extension; (b) a reamer shaft base extending from a first end to a second end and having a length of less than 23 inches, the reamer shaft base defining a second opening therein and comprising: (i) a male dovetail disposed at the first end of the second reamer shaft and configured to be removeably connected with the female dovetail of the reamer shaft extension, and (ii) a shank disposed at the second end of the reamer shaft base and configured to be removably received within a drill; wherein the first opening and second opening are coaxial when the male dovetail of the reamer shaft base is disposed in the female dovetail of the reamer shaft extension.

EXAMPLE 11

The reamer shaft extension of example 10, wherein the shaft of the reamer shaft extension comprises cutouts such that the shaft is flexible.

EXAMPLE 12

The reamer shaft extension of either example 10 and 11, wherein the reamer shaft extension comprises a substantially constant diameter from the first end to the second end.

EXAMPLE 13

A method of operating a reamer shaft extension assembly comprising at least two reamer shaft extensions, wherein each reamer shaft extension comprises a first coupling at a first end and a second coupling at a second end, the method comprising: (a) positioning each reamer shaft extension along a longitudinal axis such that the first coupling of one reamer shaft extension is aligned with the second coupling of another reamer shaft extension; and (b) assembling the first coupling of the one reamer shaft extension with the second coupling of the other reamer shaft extension; wherein the reamer shaft extension assembly has a substantially constant outer diameter along the length of the reamer shaft extension assembly.

EXAMPLE 14

The method of example 13, wherein assembling the first coupling of the one reamer shaft extension with the second coupling of the other reamer shaft extension comprises inserting a male dovetail of the first coupling into a female dovetail of the second coupling.

EXAMPLE 15

The method of example 14, further comprising positioning at least one reaming head of the female dovetail against a portion of the male dovetail to maintain the position of the male dovetail relative to the female dovetail.

EXAMPLE 16

The method of any of examples 13 through 15, further comprising adjusting a length of the reamer shaft extension assembly by adding or removing one of the reamer shaft extensions from the reamer shaft extension assembly.

EXAMPLE 17

The method of any of examples 13 through 16, further comprising positioning the reamer shaft extension assembly over a guidewire and operating the reamer shaft extension assembly to perform a reaming procedure.

EXAMPLE 18

The method of any of examples 13 through 17, further comprising disassembling the reamer shaft extension assembly by decoupling the first coupling from the second coupling.

EXAMPLE 19

The method of example 18, further comprising translating a male dovetail of the first coupling out of a female dovetail of the second coupling.

EXAMPLE 20

The method of example 18, further comprising positioning each reamer shaft extension within a sterilization tray and sterilizing each reamer shaft extension.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A reamer shaft extension assembly, comprising:
   at least two reamer shaft extensions,
   wherein each reamer shaft extension comprises a male dovetail at a first end and a female dovetail at a second end,
   wherein each male dovetail comprises a rounded end extending from a flange,
   wherein each female dovetail defines a rounded recess extending from a channel,
   wherein each female dovetail comprises at least one insert extending into the channel, and
   wherein, when the male dovetail of one of the at least two reamer shaft extensions is inserted into the female dovetail of another adjacent of the at least two reamer shaft extensions, the at least one insert is configured to compress against the flange to hold the flange within the channel and the reamer shaft extension assembly has a substantially constant outer diameter along the length of the reamer shaft extension assembly.

2. The reamer shaft extension assembly of claim 1 wherein each male dovetail comprises a first pair of tapered walls, and wherein each female dovetail comprises a second pair of tapered walls corresponding to the first pair of tapered walls.

3. The reamer shaft extension assembly of claim 1, wherein each reamer shaft extension comprises an opening extending along a longitudinal axis of the reamer shaft extension.

4. The reamer shaft extension assembly of claim 1, wherein each reamer shaft extension has a length of less than 23 inches.

5. The reamer shaft extension assembly of claim 1, wherein each reamer shaft extension is positionable in a sterilization tray for a sterilization process.

6. The reamer shaft extension assembly of claim 1, wherein each reamer shaft extension is flexible.

7. The reamer shaft extension assembly of claim 6, wherein each reamer shaft extension defines a helical cutout at least partially between the first end and the second end so that each reamer shaft extension is flexible.

8. The reamer shaft extension assembly of claim 1, wherein the at least one insert is formed from a thermoplastic material.

9. A reamer shaft extension assembly, comprising:
   a reamer shaft extension extending from a first end to a second end, the reamer shaft extension defining a first opening therethrough and comprising:
     a male dovetail disposed at the first end of the reamer shaft extension, and
     a female dovetail disposed at the second end of the reamer shaft extension, the female dovetail defining a channel comprising at least one insert extending into the channel; and
   a reamer shaft base extending from a first end to a second end, the reamer shaft base defining a second opening therein and comprising:
     a male dovetail disposed at the first end of the reamer shaft base and configured to be removably connected with the female dovetail of the reamer shaft extension, wherein the at least one insert is configured to compress against the male dovetail of the reamer shaft base to hold the reamer shaft base within the channel of the female dovetail of the reamer shaft extension when the male dovetail of the reamer shaft base is connected with the female dovetail of the reamer shaft extension, and
     a shank disposed at the second end of the reamer shaft base and configured to be removably received within a drill.

10. The reamer shaft extension assembly of claim 9, wherein the reamer shaft extension defines a helical cutout at least partially between the first end and the second end of the reamer shaft extension such that the reamer shaft extension is flexible.

11. The reamer shaft extension assembly of claim 9, wherein the reamer shaft extension has a substantially constant diameter from the first end to the second end of the reamer shaft extension.

12. The reamer shaft extension assembly of claim 9, further comprising a reamer tip at the first end of the reamer shaft extension.

13. The reamer shaft extension assembly of claim 9, wherein the first opening and the second opening are coaxial when the male dovetail of the reamer shaft base is connected to the female dovetail of the reamer shaft extension.

14. The reamer shaft extension assembly of claim 9, wherein the at least one insert is formed from a thermoplastic material.

15. The reamer shaft extension assembly of claim 9, wherein the reamer shaft extension has a length of less than 23 inches.

16. A method of operating a reamer shaft extension assembly comprising at least two reamer shaft extensions, wherein each reamer shaft extension of the at least two reamer shaft extensions comprises a male dovetail at a first end and a female dovetail at a second end, the female dovetail defining a channel comprising at least one insert extending into the channel, the method comprising:
  inserting the male dovetail of one reamer shaft extension within the female dovetail of another adjacent reamer shaft extension, wherein the at least one insert is configured to compress against the male dovetail to hold the male dovetail within the female dovetail.

17. The method of claim 16, further comprising positioning the reamer shaft extension assembly over a guidewire and operating the reamer shaft extension assembly to perform a reaming procedure.

18. The method of claim 16, further comprising disassembling the reamer shaft extension assembly by decoupling the at least two reamer shaft extensions.

19. The method of claim 18, further comprising positioning each reamer shaft extension within a sterilization tray and sterilizing each reamer shaft extension.

\* \* \* \* \*